(12) United States Patent  
Scholten et al.

(10) Patent No.: US 8,567,302 B2  
(45) Date of Patent: Oct. 29, 2013

(54) COMPRESSED GAS OPERATED INSTRUMENT, IN PARTICULAR A SURGICAL INSTRUMENT

(75) Inventors: Thomas Scholten, Tuttlingen (DE); Rupert Mayenberger, Rielasingen (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 13/349,692

(22) Filed: Jan. 13, 2012

(65) Prior Publication Data

US 2012/0180471 A1 Jul. 19, 2012

Related U.S. Application Data

(63) Continuation of application No. PCT/EP2009/065112, filed on Nov. 13, 2009.

(30) Foreign Application Priority Data

Jul. 17, 2009 (DE) .......................... 10 2009 033 525

(51) Int. Cl.  
*G05D 16/04* (2006.01)  
*F16K 31/12* (2006.01)

(52) U.S. Cl.  
USPC ................... 91/446; 137/115.26; 137/505.11; 137/505.25; 137/508

(58) Field of Classification Search  
USPC .................. 91/446; 137/505.25, 505.11, 508, 137/115.26  
See application file for complete search history.

(56) References Cited

U.S. PATENT DOCUMENTS

| | | | | |
|---|---|---|---|---|
| 393,501 | A * | 11/1888 | Delafield | 137/505.25 |
| 3,662,939 | A | 5/1972 | Bryan | |
| 3,815,476 | A | 6/1974 | Green et al. | |
| 3,837,555 | A | 9/1974 | Green | |
| 4,331,277 | A | 5/1982 | Green | |
| 4,709,697 | A | 12/1987 | Muller | |
| 5,399,159 | A | 3/1995 | Chin et al. | |
| 7,578,311 | B2 * | 8/2009 | Zaiser et al. | 137/505.25 |
| 2004/0230157 | A1 | 11/2004 | Perry et al. | |
| 2006/0069395 | A1 | 3/2006 | Lebet | |
| 2006/0112944 | A1 | 6/2006 | Su | |

FOREIGN PATENT DOCUMENTS

| | | |
|---|---|---|
| DE | 31 48 619 | 9/1985 |
| DE | 203 18 275 | 3/2004 |
| DE | 20 2006 008 404 | 8/2006 |
| DE | 20 2007 006 801 | 8/2007 |
| DE | 10 2006 024 759 | 1/2008 |

* cited by examiner

*Primary Examiner* — F. Daniel Lopez  
(74) *Attorney, Agent, or Firm* — Lipsitz & McAllister, LLC

(57) ABSTRACT

A compressed gas operated instrument incorporating a connector for a compressed gas cartridge to which the compressed gas cartridge is connectable in sealed manner by means of a supply channel for the compressed gas flowing out of the compressed gas cartridge is provided which incorporates a regulating valve in the supply channel for governing the compressed gas stream through the supply channel. The regulating valve comprises a valve body which is sealed in a valve chamber with respect to a wall of the valve chamber by means of a first seal and is mounted in the valve chamber in displaceable manner. The valve body is connected on the upstream side thereof in sealed manner to a connector element by means of a second seal and also be displaceable with respect to the connector element by displacement thereof in the valve chamber.

19 Claims, 13 Drawing Sheets

COMPRESSED GAS OPERATED INSTRUMENT, IN PARTICULAR A SURGICAL INSTRUMENT

This application is a continuation of international application number PCT/EP2009/065112 filed on Nov. 13, 2009 and claims the benefit of German application No. 10 2009 033 525.0 of Jul. 17, 2009.

The present disclosure relates to the subject matter disclosed in international application number PCT/EP2009/065112 of Nov. 13, 2009 and German application No. 10 2009 033 525.0 of Jul. 17, 2009, which are incorporated herein by reference in their entirety and for all purposes.

BACKGROUND OF THE INVENTION

The invention relates to a compressed gas operated instrument and in particular to a surgical instrument having a connector for a compressed gas cartridge to which the compressed gas cartridge is connectable in sealed manner by a supply channel for the compressed gas flowing out of the compressed gas cartridge, and also comprising a regulator valve in the supply channel which governs the stream of compressed gas flowing through the supply channel.

A medical instrument which is operated by means of a compressed gas cartridge is described in DE 20 2007 006 801 U1 for example. The connection between the interior of the gas cartridge and the supply channel of the instrument is obtained therein by means of a tapping plug through which the compressed gas flows out of the compressed gas cartridge into the supply channel. Since the pressure in the compressed gas cartridge is normally considerably higher than the pressure needed for the operation of the instrument, it is necessary for the pressure to be reduced and this can be effected with the help of a regulating valve which is coupled into the supply channel.

The object of the invention is to construct an instrument of the type mentioned in the preamble of the main Claim in such a way that the regulation of the gas pressure required for the operation of the instrument can be effected by simple means requiring very little space.

SUMMARY OF THE INVENTION

In accordance with the invention, this object is achieved in the case of a compressed gas operated instrument of the type described hereinabove in that the regulating valve comprises a valve body which is mounted in a valve chamber through which the supply channel extends, said valve body being displaceable in the valve chamber and sealed with respect to the wall of the valve chamber by means of a first seal, in that the valve body is connected on the upstream side thereof in sealed manner to a connector element by means of a second seal and is also displaceable with respect to the connector element by displacement thereof in the valve chamber, in that the connector element comprises a continuous flow channel and is connected at the inlet end thereof to the supply channel in sealed manner, in that the valve body comprises a flow passage which is connected at the outlet end thereof to the supply channel located downstream of the valve chamber, in that the valve body is displaceable in the valve chamber against the direction of flow between an open position in which there is a flowing connection between the flow channel of the connector element and the flow passage of the valve body and a closed position in which the valve body is seated in sealed manner on the flow channel of the connector element thereby closing it, in that the valve body is biased in the direction of the open position by a spring element, and in that the cross-sectional area of the valve body surrounded by the first seal is larger than the cross-sectional area surrounded by the second seal.

This arrangement leads to the effect that upon the initial connection of a compressed gas cartridge, compressed gas can flow through the supply channel and also through the valve chamber since the valve body is being held in the open position by the spring element. As soon as the pressure rises however, the pressure difference that is effective on the valve body becomes greater since the cross-sectional area surrounded by the second seal is smaller than the cross-sectional area surrounded by the first seal. Upon exceeding a certain value, the difference in force that acts on the valve body by the compressed gas becomes greater than the force of the spring element displacing the valve body into the open position whereupon the valve body is then displaced into the closed position and in this way closes the flow channel in the connector element. In consequence, a further increase of pressure downstream of the valve body is no longer possible but the pressure in this area continues to diminish due to the flow of gas escaping into the instrument until the force of the spring element again exceeds the difference of force exerted by the compressed gas on the valve body whereupon the valve body is displaced into the open position once again.

In this way, limitation of the pressure is achieved automatically by simple means, as soon as the pressure of the compressed gas in the supply channel exceeds a certain value, the supply channel is blocked, when the pressure falls back below a certain value, re-opening thereof occurs and a fresh supply of compressed gas is delivered from the compressed gas cartridge.

It is expedient if the spring element is a disc spring, one thereby obtains a large spring force whilst occupying little space.

In a preferred embodiment, provision is made for the valve body to comprise a central bearing chamber which is open at the gas inlet end and into which there enters a displaceable bearing stem of the connector element that is sealed by means of the second seal, and for the flow passage to emerge from the bearing chamber at the gas outlet end thereof. This results in a telescoping, sealed connection between the bearing stem of the connector element on the one hand and the valve body on the other.

It is expedient, if the valve body abuts against the gas outlet end face of the connector element in the closed position thereof and thereby closes the flow channel.

Furthermore, in a particularly preferred embodiment, provision is made for the connector element to be pressed by a spring element into a sealing position in which the connector element abuts tightly against the supply channel entering the valve chamber and thereby connects said supply channel in gas-tight manner to the flow channel in the connector element, and for said element to be displaceable against the effect of the spring element from the supply channel into a disengaged position in which the supply channel entering the valve chamber is open in the part of the valve chamber that is located upstream of the first seal.

Whereas the connection between the supply channel on the one hand and the flow channel in the connector element is sealed in the sealing position, it is possible in the disengaged position for the compressed gas to escape laterally into the valve chamber and thus not enter the flow channel of the connector element, this part of the valve chamber usually being ventilated and in communication with the surroundings so that a pressure relieving process can be effected in this way. In connection therewith, the dimensions are selected in such a way that a displacement of the connector element into the disengaged position only takes place when the pressure in the compressed gas cartridge exceeds a very high value. This may be the case if, after use of the instrument, the compressed gas cartridge remains in the instrument and the instrument is passed on for a sterilization process. Due to the very high temperatures occurring during the sterilization process, pressure values can occur in the compressed gas cartridge which could lie far above the normal storage pressure and thus lead to destruction of the compressed gas cartridge. This is prevented by the displaceable connector element which thus works as a relief valve in the event of excessive pressure in the compressed gas cartridge.

It is particularly advantageous, if the spring element displacing the valve body into the open position and the connector element into the sealing position is the same spring element. This spring element thus pushes the valve body and the connector element apart into their respective end positions and is compressed both by the displacement of the valve body into the closed position and by the displacement of the connector element into the disengaged position. This thus results in the overall height of the entire assembly being particularly small.

In accordance with a preferred embodiment of the invention, provision is thereby made for the ratio of the cross-sectional area of the valve body located downstream to the cross-sectional area of the connector element located upstream to be larger than the ratio of the pressure in the compressed gas cartridge to the regulated pressure downstream of the valve body at ambient temperature and smaller than the ratio of these pressures at temperatures that are significantly higher compared with ambient temperature.

In a further preferred embodiment, provision is made for a closure body to be mounted in the supply channel downstream of the regulating valve in displaceable manner, said closure body being displaceable by a connector fitting that is inserted into the supply channel from the downstream side thereof from a closed position located downstream into an open position located upstream, for the closure body to unblock the passage through the flow channel in the open position and block it in the closed position, and for the closure body to comprise a passage of very small cross section which permits a very much reduced current of the compressed gas to flow past the closure body even when the closure body is positioned in the closed position.

In normal operation, this closure body is displaced into the open position by means of the connector fitting of the instrument that has been inserted into the supply channel and consequently does not restrict the flow through the supply channel. When the connector fitting is removed however, the closure body is moved into the closed position and blocks the cross section of the supply channel, although there is still the exception of a very small cross section through which the compressed gas can leak out to a small extent. This thereby ensures that, after use of the instrument and after the removal of the connecting piece from the supply channel, a compressed gas cartridge which has remained in the instrument will be emptied gradually. When next using the instrument, the user is thus forced to insert a new compressed gas cartridge i.e. usage is always begun with a full compressed gas cartridge. Since relatively large time periods normally occur between each individual usage, this emptying of the compressed gas cartridge can be effected very slowly, i.e. the free cross section of the closure body in the closed position can be very small, for example, the emptying of the compressed gas cartridge can be effected over several hours.

The passage may be a channel of very small cross section passing through the closure body, i.e. effectively, a very narrow throttling bore, in another embodiment, provision may be made for the passage to be formed by a porous wall region of the closure body.

It is advantageous, if the closure body is biased in the direction of the closed position by a spring. It is thereby ensured that the closure body is always displaced automatically into the closed position after removal of the connector fitting.

Furthermore, provision may be made for the closure body to be sealed with respect to the supply channel by means of a seal when it is in the closed position.

The following description of preferred embodiments of the invention taken in conjunction with the drawing serves for a more detailed explanation.

DETAILED DESCRIPTION OF THE INVENTION

Figure 11:
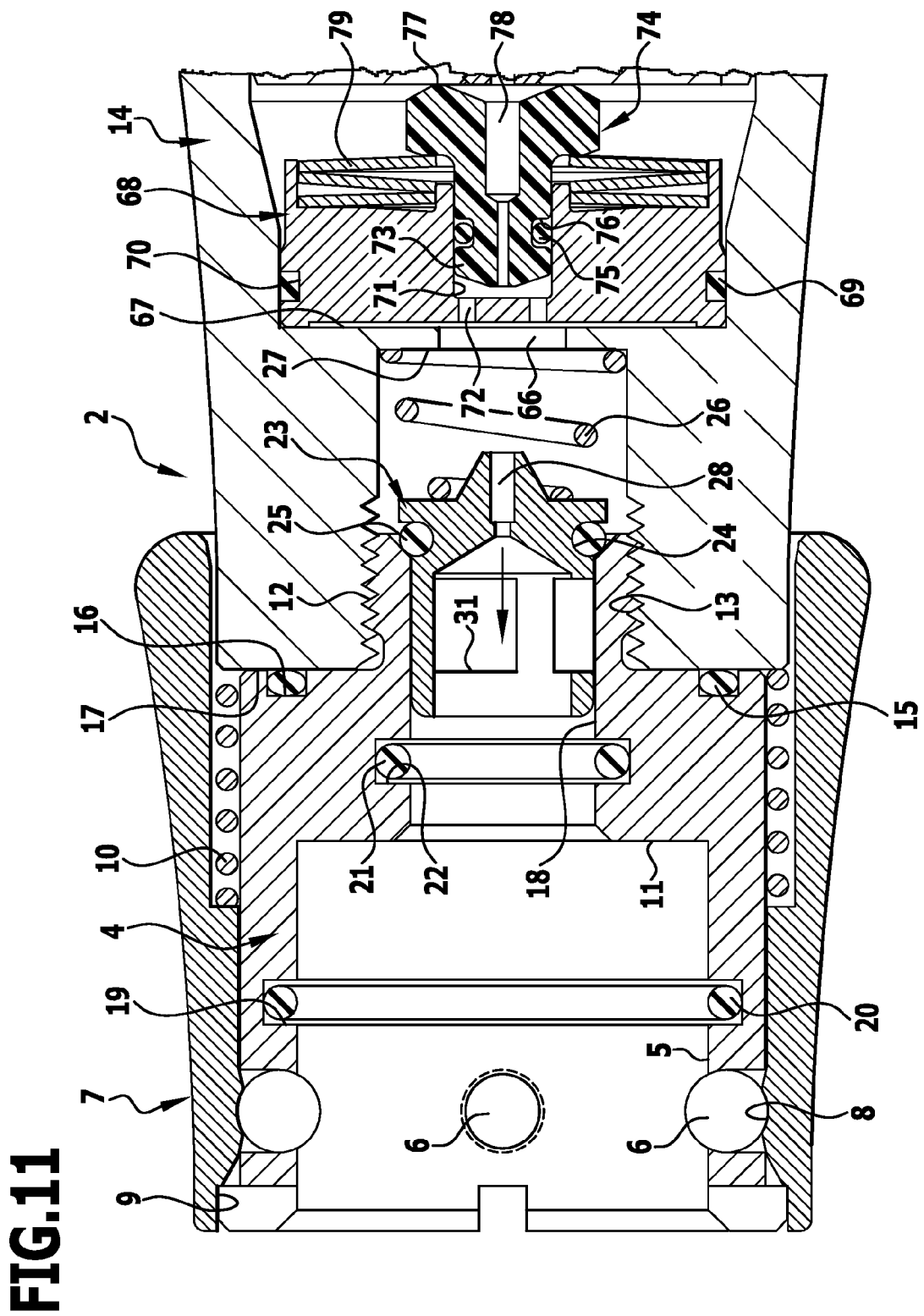
FIG. 11: an enlarged sectional view of the outlet end of the connector with the closure body in the closed position.

In the drawing, there is illustrated a compressed gas supply for an instrument, especially a medical instrument such as an instrument for placing staples, for driving a cutting tool or the like for example. Of this instrument however, only a tubular connector fitting 1 which is connected by a connector 2 to a compressed gas cartridge 3 is illustrated in the drawing. This connector is described in more detail hereinafter although it is self evident that this connector can be connected by a connector fitting 1 to any compressed gas operated instrument. For this purpose, the connector comprises a plug-in bushing 4 incorporating a cylindrical plug-in chamber 5, whereby the likewise cylindrical connector fitting 1 can be pushed into this plug-in chamber 5 from one side and fixed therein in the axial direction with the help of spherical locking elements 6 that are mounted in the plug-in bushing 4 in radially displaceable manner. These locking elements 6 can be moved between a radially pushed-in position in which they are located in corresponding depressions in the connector fitting 1, and a radially pushed-out release position in which they have been displaced outwardly to such an extent that the connector fitting 1 can be pushed freely into the plug-in chamber 5 and pulled out again therefrom. For the purposes of fixing the spherical locking elements 6 in the pushed-in locking position thereof, there is provided a sleeve 7 consisting of two neighbouring sections 8, 9 of differing internal diameters which surround the plug-in bushing 4 and are axially displaceable with respect thereto. When placed on the section 8 of smaller internal diameter, the spherical locking elements 6 are displaced radially inwards, whereas when the spherical locking elements 6 are placed on the section 9 of larger internal diameter they can be displaced radially outwards. The sleeve 7 is displaced by a coil spring 10 surrounding the plug-in bushing 4 in such a way that the section 8 of smaller internal diameter covers the spherical locking elements 6. In order to enable these spherical locking elements 6 to be released, the sleeve 7 must be pushed back radially against the effect of the coil spring 10 (FIG. 11).

At the end thereof opposite the open end of the plug-in chamber 5, the plug-in bushing 4 carries a central externally threaded connector 12 with which the plug-in bushing 4 is screwed into an internally threaded bore 13 in a central connecting piece 14. Hereby, the plug-in bushing 4 is sealed with respect to the central connecting piece 14 by means of a ring seal 15 which is arranged in an annular groove 16 in the rear face of the plug-in bushing 4 and abuts the end face 17 of the central connecting piece 14.

The plug-in chamber 5 merges, forming a step 11, into a central flow channel 18 which passes centrally through the externally threaded adapter 12. A ring seal 20 is inserted into a peripheral groove 19 in the inner wall of the plug-in chamber 5, whilst a further ring seal 21 is inserted into a peripheral groove 22 in the inner wall of the central flow channel 18.

A closure body 23 which is displaceable in the longitudinal direction of the flow channel 18 is inserted into the central flow channel 18, said body partially protruding from the externally threaded adapter 12 and having an external diameter at this point which is larger than the internal diameter of the central flow channel 18. In this region, a ring seal 25 is inserted into a peripheral groove 24 in the closure body 23, said ring seal abutting the outer edge of the central flow channel 18 when one displaces the closure body in the direction of the plug-in chamber 5. The closure body 23 thus shuts off the flow channel 18 in this position, this position being referred to as the closed position. The closure body is pressed into this position by a coil spring 26 which is supported on the outer face of the closure body 23 on the one hand and on a step 27 of the connecting piece 14 on the other.

A passage 28 in the form of a bore of very small diameter is arranged in the closure body 23. This passage 28 thus connects the interior of the connecting piece 14 to the central flow channel 18. However, the diameter is so small that only a very small quantity of gas can pass therethrough per unit of time, although the diameter of this passage 28 is depicted as being relatively large in the drawing for illustrative purposes. In connection therewith, in reality, it can be an extremely narrow bore or even a porous wall section in the rear face of the closure body which permits an excess gas pressure to ebb away slowly from the interior of the connecting piece 14 in the direction of the open plug-in chamber 5.

Figure 1:
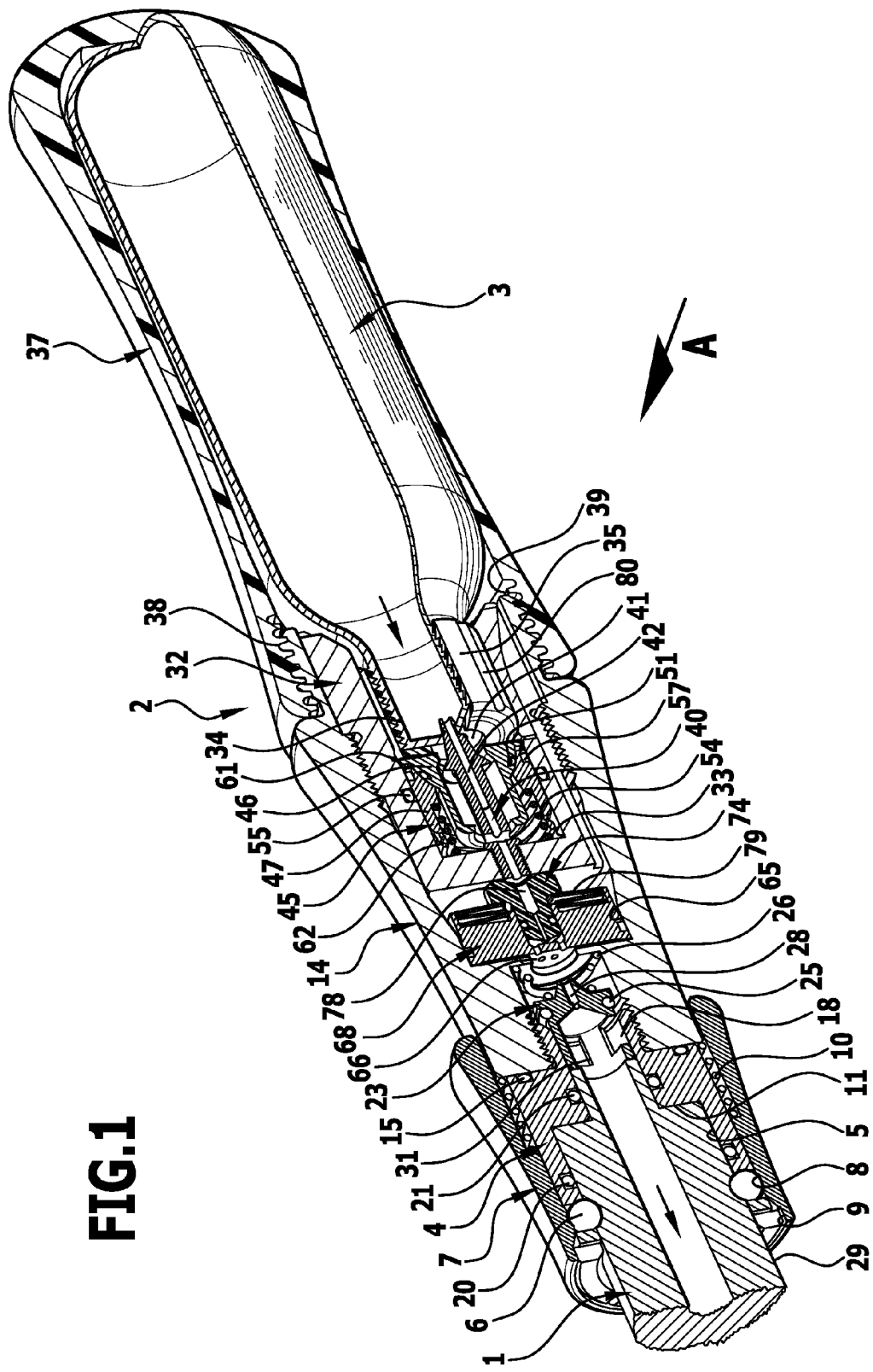
FIG. 1: is a perspective longitudinal sectional view of a connector of a compressed gas cartridge having a compressed gas cartridge inserted therein.

The connector fitting 1 of an instrument comprises a first section 29 having an external diameter which corresponds to the internal diameter of the plug-in bushing 4, and a second section 30 having a substantially smaller external diameter which corresponds to the internal diameter of the central flow channel 18 (FIG. 1). When inserting the connector fitting 1 into the plug-in bushing 4, the section 29 is accommodated in the plug-in bushing 4, whereas the section 30 is accommodated in the central flow channel 18. In this connection, the section 30 of the connector fitting 1 pushes the closure body 23 out of the central flow channel 18 against the effect of the coil spring 26 into an open position in which the ring seal 25 is lifted off the edge of the central flow channel 18 so that the closing effect in this region is terminated. Window openings 31 are arranged in the side wall of the closure body 23, said openings establishing a connection between the interior of the connector fitting 1 on the one hand and the interior of the connecting piece 14 on the other as soon as the closure body 23 is located in the open position. Consequently, the flow of gas from the interior of the connecting piece 14 into the interior of the connector fitting 1 is not obstructed in this position.

Such an obstruction only occurs when the closure body is in the closed position once more, this presupposing that the connector fitting 1 has been removed from the plug-in bushing 4, as is illustrated in FIG. 11. It is only in this position that the passage 28 becomes effective at all. In the open position, the cross section of the passage 28 is so small with respect to the remaining cross-sectional areas for the flow of the gas that it is of no practical consequence. In the closed position on the other hand, as a result of the passage 28, there is no hermetic closure, but the pressure in the interior of the connecting piece 14 can gradually diminish due to this passage 28 whereby the duration of this pressure reduction process is dependent on the cross section of the passage 28.

Figure 12:
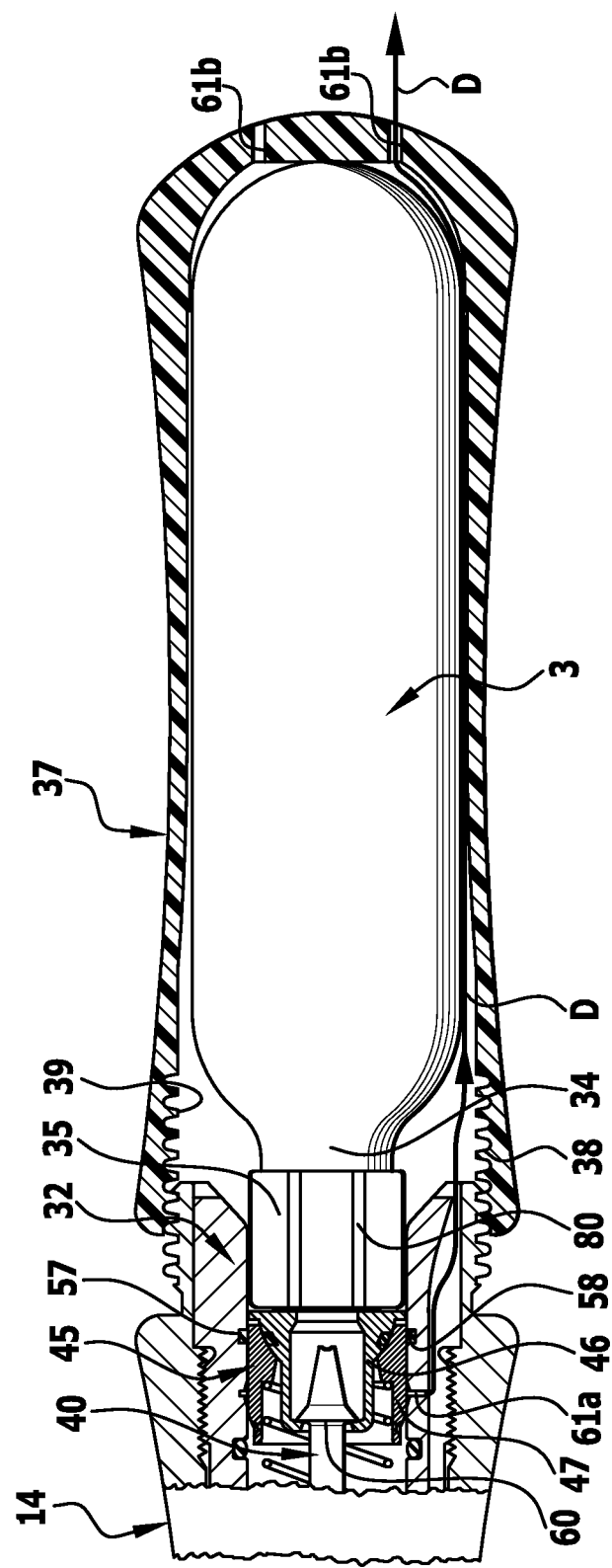
FIG. 12: a sectional view of the compressed gas cartridge with the compressed gas cartridge in the correctly mounted direction
Figure 13:
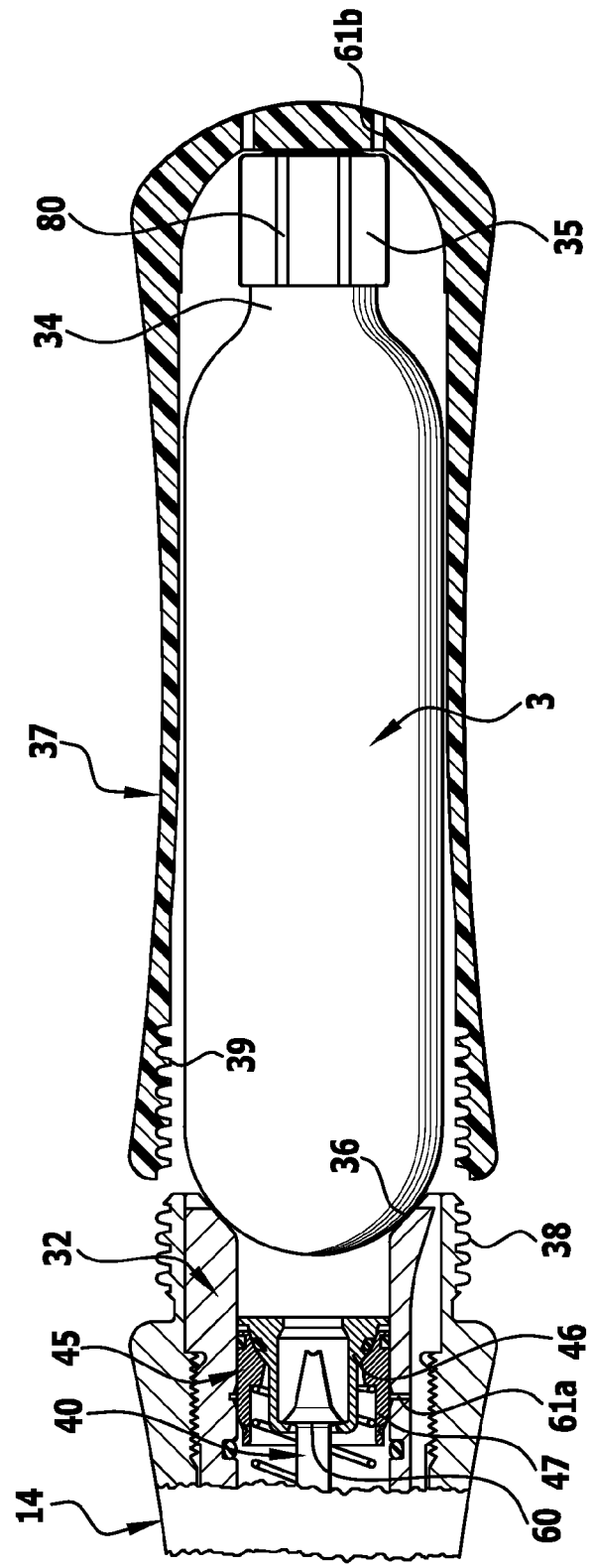
FIG. 13: a sectional view similar to FIG. 9 with the compressed gas cartridge in the wrongly mounted direction.

A cup-shaped seating body 32 is screwed into the connecting piece 14 at the side thereof opposite the plug-in bushing 4. The open interior of the seating body 32 at the rear end of the connecting piece 14 forms a connector shaft 33 for the cylindrical connector region 34 of the compressed gas cartridge 3. This cylindrical compressed gas cartridge 3 is rounded off in spherical manner at the rear end thereof, whereas at the front end thereof, it ends in the manner of the neck of a bottle in a cylindrical connector region 34 which is covered by a sealing cap 35 consisting of a ductile plastic material. The connector region 34 of the compressed gas cartridge 3 can be pushed into the connector shaft 33, the insertion depth being limited by virtue of that region of the compressed gas cartridge 3 of larger external diameter hitting the correspondingly formed rim 36 of the seating body 32. Another aspect of this rim 36 is that it also prevents the compressed gas cartridge 3 from being inserted into the connector shaft 33 the wrong way round, i.e. with the spherical end at the front as is illustrated in FIG. 12. In this case, the spherical end hits the rim 36 and thus prevents the compressed gas cartridge from getting any closer to the connecting piece 14 and thereby damaging the tapping plug 40 (see below).

The compressed gas cartridge 3 can be fixed in position on the connecting piece 14 by means of a covering sleeve 37. To this end, the rear end of the connecting piece 14 carries an external thread 38 onto which the covering sleeve 37 can be screwed by means of its internal thread 39. Hereby, the dimensions are selected in such a way that, when correctly oriented, the covering sleeve 37 will push the compressed gas cartridge 3 against the connecting piece 14 until such time as the larger external diameter region of the compressed gas cartridge 3 abuts against the rim 36 of the seating body 32. In the event that the compressed gas cartridge is wrongly oriented, it remains so far in front of the connecting piece 14 that the internal thread 39 of the covering sleeve being pushed over the wrongly oriented compressed gas cartridge 3 cannot reach the external thread 38. Consequently, it is not possible to screw the covering sleeve 37 thereon. This serves as a means for checking the correct orientation of the compressed gas cartridge 3 relative to the connecting piece 14.

Figure 2:
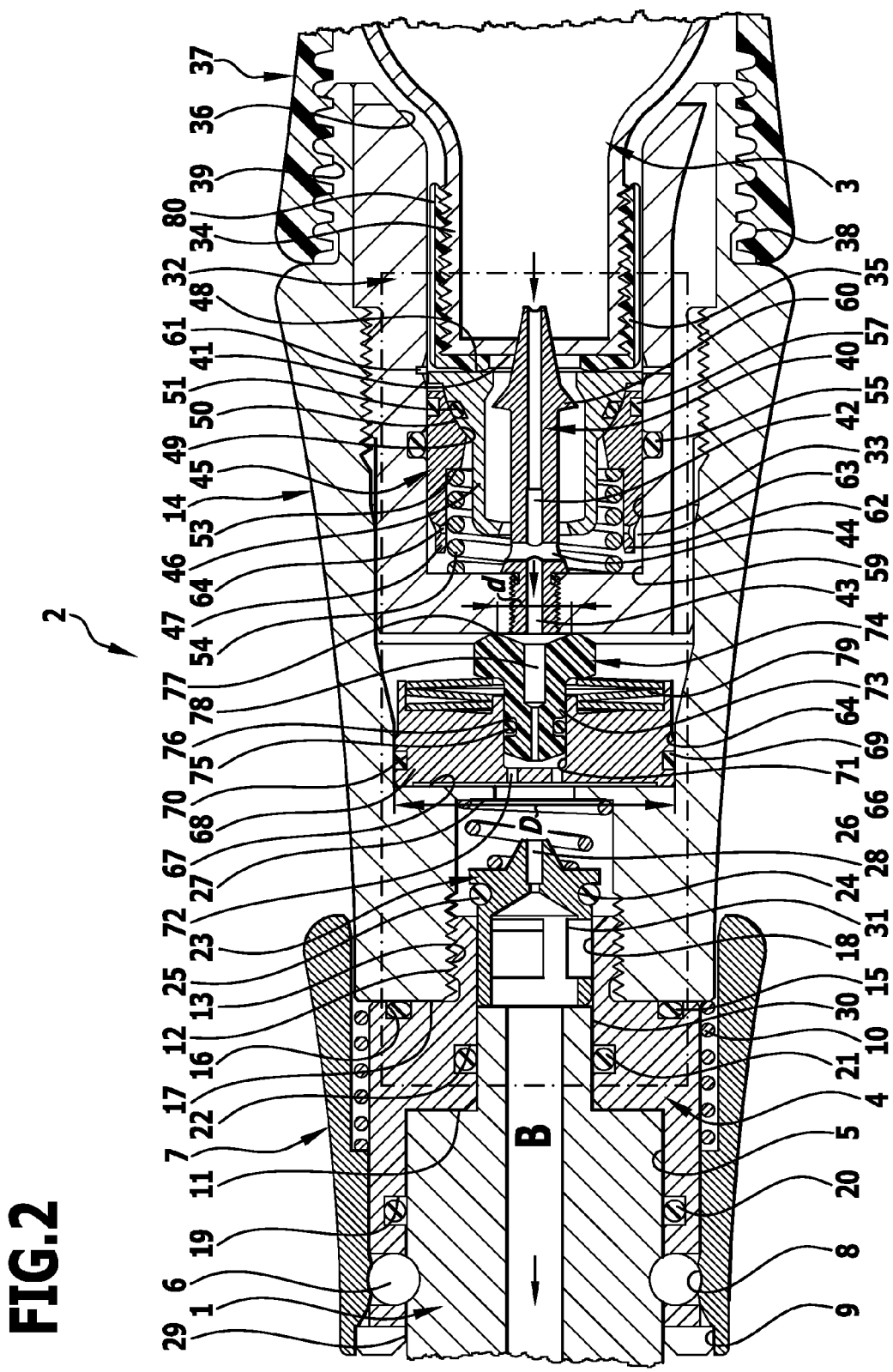
FIG. 2: a partial view of the connecting part depicted in FIG. 1 in the direction of the arrow A in FIG. 1.
Figure 3:
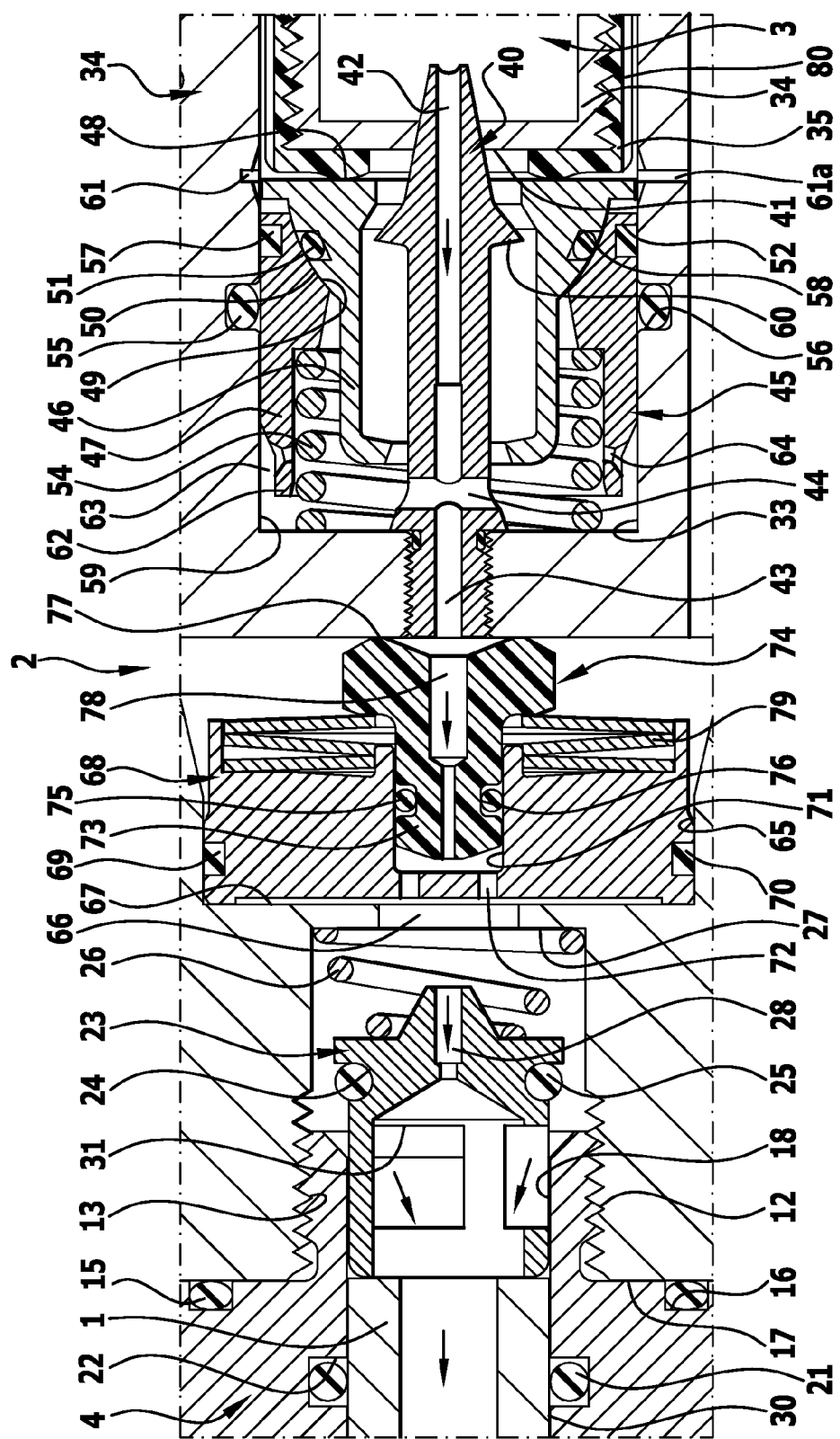
FIG. 3: a detail view corresponding to the detail B in FIG. 2 with the regulating valve in the open position thereof.

A central tapping plug 40, which is mounted such that it is not displaceable with respect to the seating body 32 in the axial direction, is arranged in the connector shaft 33, for example, it is screwed into the base of the connector shaft. This tapping plug 40 protrudes from the base of the connector shaft 33 to such an extent that it perforates the end face 41 of the compressed gas cartridge 3 when the compressed gas cartridge 3 is inserted fully into the connector shaft 33 (FIGS. 2 and 3).

A tubular channel 42 passes through the tapping plug 40, this channel forming part of the overall flow channel extending from the interior of the compressed gas cartridge 3 up to the connector fitting 1, i.e. it is a part of a supply channel 43 for the compressed gas passing through the connecting piece 14. Moreover, the channel 42 in the tapping plug 40 is coupled to the interior of the connector shaft 33 via a transverse bore 44.

In the connector shaft 33, there is arranged a sealing piece 45 which consists of two parts, namely a hat-like inner part 46 and a sleeve-like outer part 47, said sealing piece surrounding but being spaced from the tapping plug 40 and being mounted in the connector shaft 33 such that it is displaceable in the longitudinal direction thereof. At the end of the inner part 46 facing the compressed gas cartridge 3, the inner part 46 comprises an end face sealing surface 48 which abuts in sealing manner on the sealing cap 35 when the compressed gas cartridge 3 has been inserted, and, for the purposes of improving the sealing effect in the sealed region, this sealing cap 35 can be widened out in the form of a bead.

The sleeve-like outer part 47 is supported by means of a spherical-shaped inner surface 49 thereof on a likewise spherical-shaped outer surface 50 of the inner part 46, and in this region, the inner part 46 and the outer part 47 are mutually sealed by means of a ring seal 51 which is inserted into a peripheral groove 52 in the outer surface 50. A coil spring 54 surrounding and spaced from the tapping plug 40 is supported on a step 53 of the outer part 47, the other end thereof abutting against the base of the seating shaft 33 and thus loading the outer part 47 in the direction of the compressed gas cartridge 3. The inner part 46 is thereby also displaced in the same direction since the inner surface 49 of the outer part 47 is abutting against the outer surface 50 of the inner part 46. The coil spring 54 thereby pushes the entire sealing piece 45 against the end face 41 of the compressed gas cartridge 3 which is inserted into the connector shaft 33 and thereby presses the sealing surface 48 against the sealing cap 35 so that a sealing effect takes place in this region.

The outer part 47 of the sealing piece 45 is likewise sealed with respect to the inner wall of the connector shaft 33, namely, by means of a ring seal 55 which is inserted into a peripheral groove 56 in the inner wall of the connector shaft 33 and abuts against the outer surface of the outer part 47 on the one hand, and by means of a ring seal 57 which is inserted into a peripheral groove 58 in the outer surface of the outer part 47 and abuts against the inner wall of the connector shaft 33 on the other. The sealing process within this region could also be effected by a ring seal which is worked into a peripheral groove in the inner wall of the connector shaft 33 so that the ring seal would then be placed in sealing manner on the outer surface of the outer part 47 as is illustrated in FIG. 12.

The sealing piece 45 is sealed with respect to the inner wall of the connector shaft 33 by means of the sealing process described, thereby resulting in a sealed section 59 of the connector shaft 33 which is arranged downstream of the sealing piece 45 as seen from the compressed gas cartridge 3.

Prior to insertion of the compressed gas cartridge 3, this sealing piece 45 is located in the connector shaft 33 in a rest position wherein the coil spring 54 is at least partly relaxed so that the hat-shaped inner part 46 abuts on a projection 60 on the outer surface of the tapping plug 40 which thereby limits the displacement of the sealing piece 45. When a compressed gas cartridge 3 is inserted, it then pushes the sealing piece 45 out of its rest position, against the effect of the coil spring 54, into the sealing position in which the coil spring 54 presses the sealing piece 45 against the sealing cap 35 of the compressed gas cartridge 3.

The cross-sectional area of the sealing piece 45 surrounded by the seal between the sealing cap 35 and the sealing surface 48 is smaller than the cross-sectional area surrounded by the ring seals 55 and 57 so that, due to the build-up of pressure in the section 59 of the connector shaft 33 that is sealed-off by the sealing piece 45, a differential force is exerted on the sealing piece 45 which reinforces the effect of the coil spring 54. This differential force increases with increasing pressure in the section 59. It thus relates to a self-reinforcing effect of the sealing piece 45.

A peripheral groove 61, which communicates externally with the surroundings, is arranged in the inner wall of the connector shaft 33. The connector shaft 33 can thus be ventilated via this peripheral groove 61. This peripheral groove 61 is offset with respect to the ring seal 55 in the direction of the open end of the connector shaft 33 so that the section 59 of the connector shaft 33 is sealed with respect to this peripheral groove 61 for as long as the sealing piece 45 is located in the sealing position. That is to say, the ring seal 55 is then abutting against the outer surface of the sealing piece 45 in sealing manner.

Figure 6:
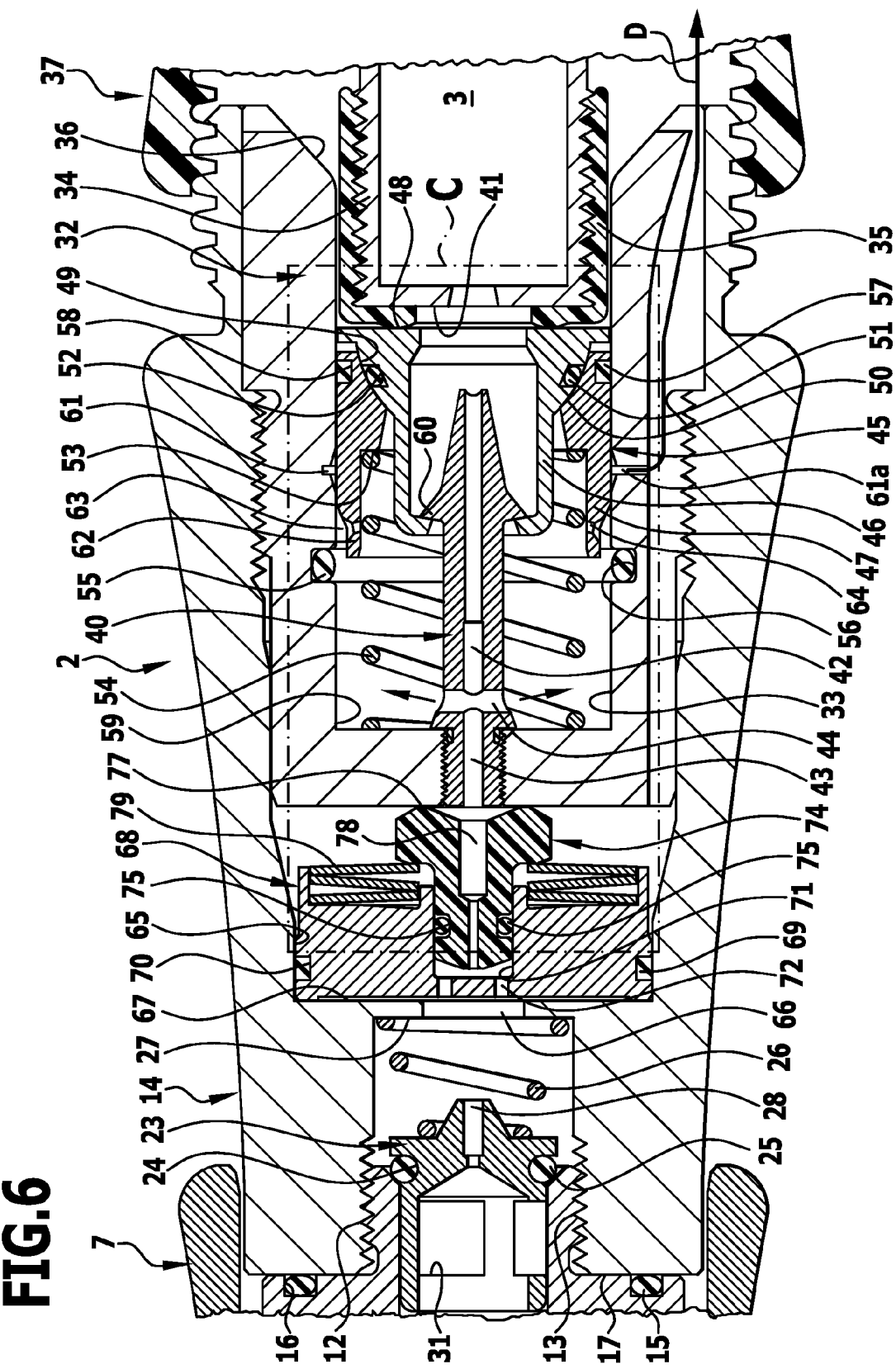
FIG. 6: a view similar to FIG. 3 but without the instrument-side connector fittings at the outlet end of the connector and with the compressed gas cartridge partly pulled out of the connector shaft.
Figure 7:
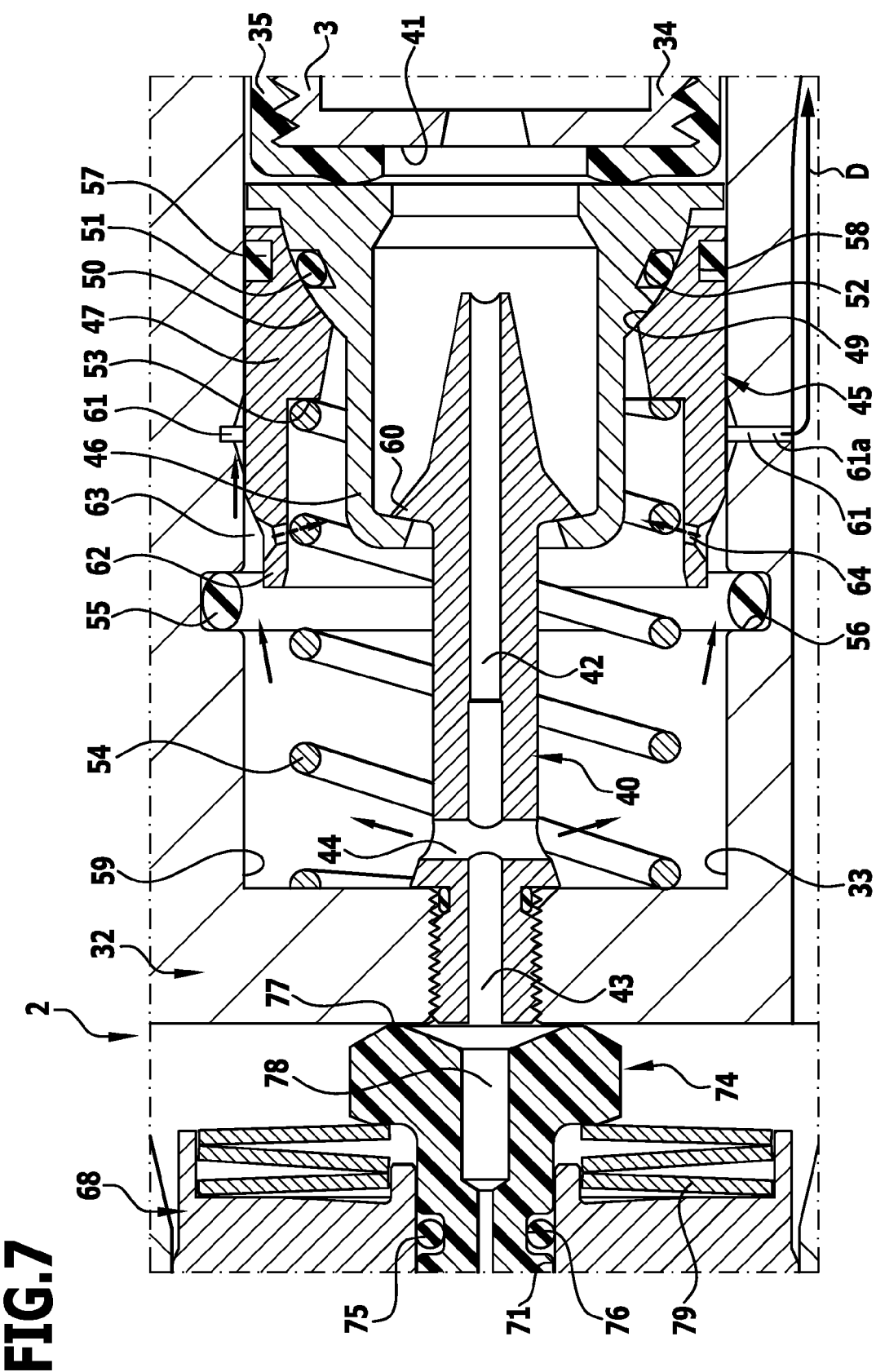
FIG. 7: a view of the detail C in FIG. 6 in the form of an enlarged illustration.
Figure 9:
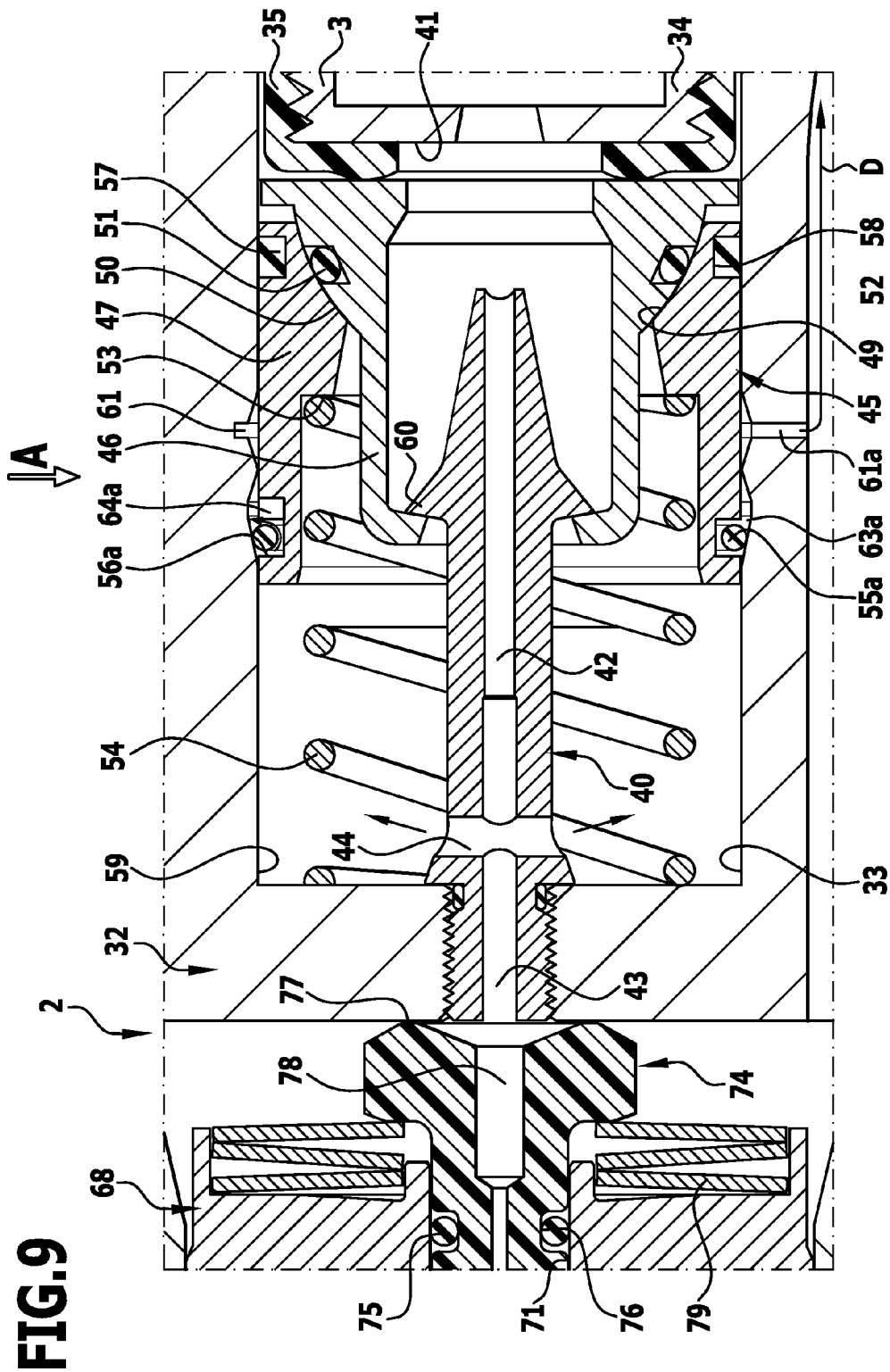
FIG. 9: a view similar to FIG. 8 with a ring seal entered into the widening in the inner wall of the connector shaft.

The peripheral groove 61 is coupled via a ventilation bore 61a to the interior which is surrounded by the connecting piece 14 on the one hand and by the covering sleeve 37 on the other. As is clear from the illustration in FIG. 12, the covering sleeve 37 at the end thereof remote from the internally threaded portion 39 has several discharge openings 61b through which the gas streaming out through the peripheral groove 61 can flow off into the surroundings. Thus here, the discharging process takes place in a region which is maximally distanced from the functional parts of the instrument and wherein there is no danger of the user grasping this region so that no discomfort to or endangerment of the user can occur. The flow path of the gas emerging via the peripheral groove 61, the ventilation bore 61a, the interior of the connecting piece 14 as well as the covering sleeve 37 and the outlets 61b is indicated in FIGS. 6 and 9 by the arrows D.

The ventilation bore 61a has a very small cross section and thus functions as a throttle point between the peripheral groove 61 and the outer space. This thus ensures that the flow rate of the emerging gas-filling is restricted, i.e. the gas-filling does not all suddenly escape at once.

At the end thereof facing the base of the connector shaft 33, the sealing piece 45 comprises a boundary region 62 having an external diameter which is smaller than the external diameter of the remaining outer surface area of the outer part 47 of the sealing piece 45. Consequently, as soon as this boundary region 62 reaches the vicinity of the ring seal 55, the sealing effect in the region of the ring seal 55 is removed, i.e. a narrow gap 63 is formed at this point between the ring seal 55 and the boundary region 62 of the outer part 47. A connection between the section 59 on the one hand and the ventilated peripheral groove 61 on the other is established by means of this gap 63 and the section 59 can be ventilated by virtue of this connection, i.e. an excess pressure developed therein can be dissipated.

Due to this dissipation process, very high flow rates can develop in the gap 63 as a result of which there is a danger that the ring seal 55 is drawn into the gap 63 and thereby damaged, moreover the flow path between the section 59 and the peripheral groove 61 would thereby be blocked. In order to prevent this from happening, the sleeve-like outer part 47 is provided in the vicinity of the boundary region 62 with radial relief bores 64 through which the gas can flow out—from the section 59 into the gap 63. In consequence, the occurrence of too large a negative pressure within this region and hence inadvertent drawing of the ring seal 55 into the gap 63 is prevented.

Figure 8:
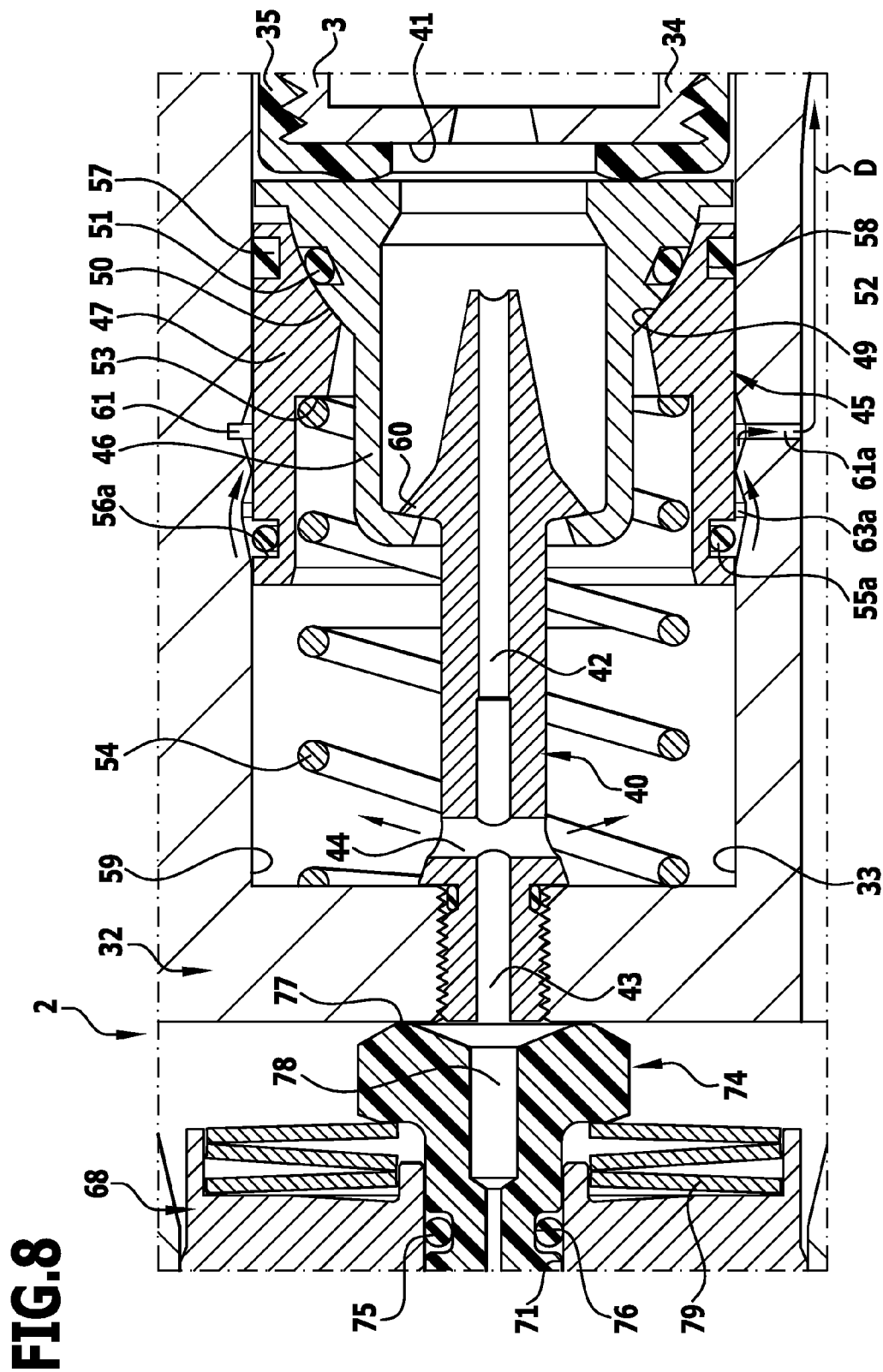
FIG. 8: a view similar to FIG. 7 in the case of a modified exemplary embodiment with a ring seal in the sealing piece and a widening in the inner wall of the connector shaft.
Figure 10:
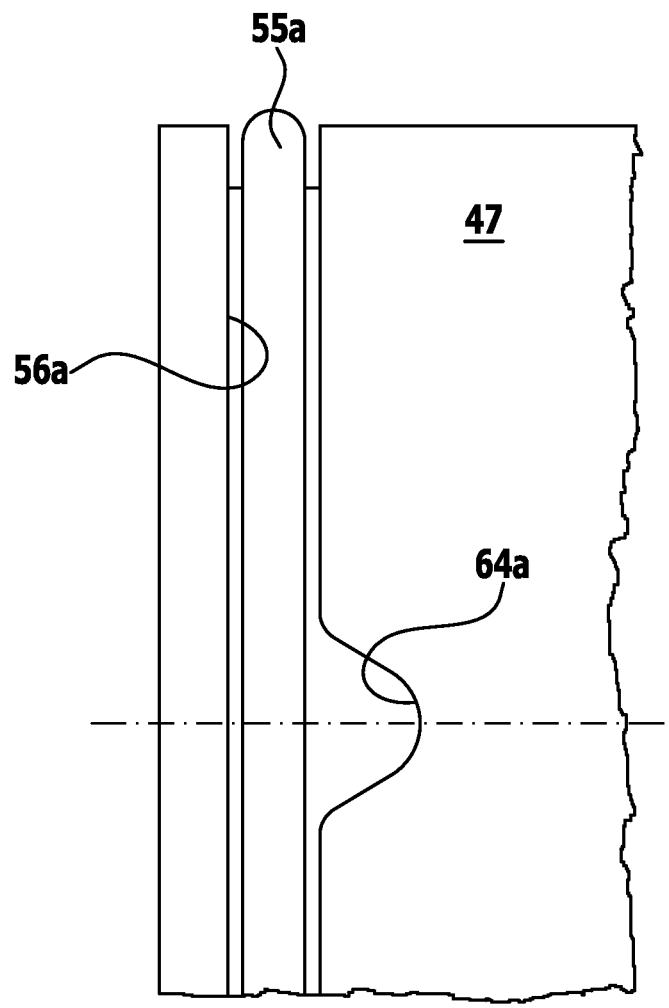
FIG. 10: a plan view of the sealing piece of FIG. 9 in the region of the ring seal with a lateral recess of the peripheral groove accommodating the ring seal.

Whereas in the exemplary embodiment of FIGS. 1 to 7 the sealing process between the sealing piece 45 and the inner wall of the connector shaft 33 is effected by means of a ring seal 55 which is inserted into a peripheral groove 56 in the inner wall of the connector shaft 33, in the exemplary embodiment of FIGS. 8 to 10, which in all other respects is constructed to a large extent in a similar manner and wherein the parts thereof are consequently provided with the same reference symbols, sealing of the sealing piece 45 with respect to the inner wall of the connector shaft 33 is achieved by means of a ring seal 55a which is inserted into a peripheral groove 56a in the outer wall of the sealing piece 45 and which normally abuts against the inner wall of the connector shaft 33 in sealing manner.

In this arrangement, a peripheral groove-like widening 63a is formed in the inner wall of the connector shaft 33, namely, in a manner such that the ring seal 55a is located opposite this widening 63a when the sealing piece 45 is in the ventilation position. As a result of the widening 63a, there is produced a flow path which leads past the ring seal 55a and connects the section 59 of the connector shaft 33 located downstream of the sealing piece 45 to the peripheral groove 61 and the ventilation bore 61a. This provision of an auxiliary flow path corresponds, in the exemplary embodiment of FIGS. 1 to 7, to the ventilation position wherein the boundary region 62 of smaller external diameter is located opposite the ring seal 55.

In the case of the exemplary embodiment illustrated in FIG. 9, the ring seal 55a could be carried along by the stream of gas flowing past it and expanded in a manner such that it would be pressed outwardly into the widening 63a and thus block the gap between the sealing piece 45 and the inner wall of the connector shaft 33. A connection for the flow of gas to the peripheral groove 61 and the ventilation bore 61a would then be disrupted. In order to prevent this from happening in the exemplary embodiment of FIGS. 9 and 10, at least one recess 64a is arranged to the side of the peripheral groove 56a, this being substantially in the form of a depression in the side wall of the peripheral groove 56a and, when the sealing piece 45 is located in the ventilation position, it ensures that the peripheral groove 56a will remain coupled to the peripheral groove 61 for the flow of gas even in the event of an expanded ring seal 55a. Even in the case where the ring seal 55a has expanded, it cannot actually block the recess 64a or the recesses 64a, which may be distributed over the periphery of the peripheral groove 56a, so that a path for the flow of gas remains free in this region.

As long as the covering sleeve 37 is screwed firmly onto the connecting piece 14 and the compressed gas cartridge 3 is thus pushed fully into the connector shaft 33, the sealing piece 45 remains in the sealing position, the peripheral groove 61 therefore remains blocked. However, as soon as the user partly unscrews the covering sleeve 37 from the connecting piece 14, the sealing piece 45 is urged in the direction of the rest position under the influence of the coil spring 54 and the pressure difference caused by the gas pressure since the compressed gas cartridge 3 is now free or is at least partially withdrawn from the connector shaft 33. Consequently, the sealing piece moves between the sealing position and the rest position into a disengaged position located therebetween in which the boundary region 62 faces the ring seal 55 and in which the peripheral groove 61 is open towards the section 59. This leads to the effect that the compressed gas can escape from the compressed gas cartridge into the surroundings, although not suddenly and all at once, but gradually, since the cross section of the peripheral groove 61 and the adjoining bore 61a are small. Thus, when unscrewing the covering sleeve 37, there is an emptying of the compressed gas cartridge 3 which occurs simultaneously with the unscrewing process but which does not involve a sudden outflow of compressed gas and the unpleasant hissing of the compressed gas associated therewith. Due to the seal produced between the sealing piece 45 and the inner wall of the connector shaft 33 by means of the ring seal 57, it is also ensured that the stream of the gas-filling flows exclusively via the peripheral groove 61 and will not emerge in an uncontrolled manner between the sealing piece 45 and the inner wall of the connector shaft 33.

Complete unscrewing of the covering sleeve 37 and thus withdrawal of the compressed gas cartridge 3 in its entirety is only possible after a few revolutions of the covering sleeve 37, the time for this being sufficient for emptying the compressed gas cartridge 3 or emptying it to at least a large extent so that the latter will be emptied or virtually emptied when the compressed gas cartridge 3 is withdrawn from the connector shaft 33.

Between the base of the connector shaft 33 on the one hand and between the step 27 of the connecting piece 14 on the other, there is a valve chamber 65 in the connecting piece 14 into which the channel 42 of the tapping plug 40 leads on the one hand and from which an outlet opening 66 surrounded by the step 27 exits on the other. This outlet opening 66 has a substantially smaller diameter than the valve chamber 65, so that a step 67 surrounding the outlet opening 66 is formed at the point of transition between the valve chamber 65 and the outlet opening 66.

In the interior of the valve chamber 65, there is a disk-shaped valve body 68 which is mounted in displaceable manner and is sealed with respect to the inner wall of the valve chamber 65 by means of a first ring seal 69 which is inserted into a peripheral groove 70 in the external wall of the valve body 68. A central bearing chamber 71 in the form of a cylindrical blind-hole bore is arranged in the valve body 68 at the end thereof facing the seating body 32, said bearing chamber being connected at the central closed end thereof through off-centre flow passages 72 to the section of the valve chamber 65 located downstream of the valve body 68 and hence to the outlet opening 66.

The cylindrical bearing stem 73 of a connector element 74 is slid into this cylindrical bearing chamber 71 and is mounted in longitudinally displaceable manner in this bearing chamber 71. A second ring seal 75, which is inserted into a peripheral groove 76 of the bearing stem 73, seals the bearing stem 73 with respect to the inner wall of the bearing chamber 71.

The connector element 74 widens-out outside the bearing chamber 71 and, in this region, it forms a ring-like sealing shoulder 77 which normally abuts in sealing manner on the rear face of the base of the seating body 32 and surrounds the outlet of the tapping plug 40 into the valve chamber 65 in sealing manner. The connector element 74 may consist of a synthetic material and it is ductile especially in the region of the sealing shoulder 77. Passing therethrough is a flow channel 78 which thereby interconnects the channel 42 in the interior of the tapping plug 40 on the one hand and the bearing chamber 71 in the region directly following the flow passages 72 on the other.

The diameter D of the valve chamber 65 and that of the valve body 68 are substantially equally large, whereas the diameter d of the sealing shoulder 77 of the connector element 74 is significantly smaller in comparison therewith (FIG. 2), for example, D=19 mm and d=6 mm, consequently, the ratio of the effective pressure-subjected surfaces of the valve body 68 and of the connector element 74 is approximately 10. These ratios can deviate, for example, the ratio d:D may lie between 1:2 and 1:4.

A disc spring 79 surrounding the connector element 74 is supported on the valve body 68 at the end thereof facing the seating body 32, said spring being supported at the opposite end thereof on the widened part of the connector element 74. This disc spring 79 thus presses the valve body 68 and the connector element 74 apart and normally presses the valve body 68 against the step 67 and the sealing shoulder 77 of the connector element 74 against the rear face of the base of the connector shaft 33 (FIG. 3). In this position, gas emerging through the tapping plug 40 from the compressed gas cartridge 3 can flow unhindered into the connector fitting 1 through the connector element 74 and the valve body 68 via the flow passages 72 and the outlet opening 66 as well as via the opened closure body 23. Hereby, the closure body 23 is in its open position, the connector element 74 in its sealing position.

Figure 4:
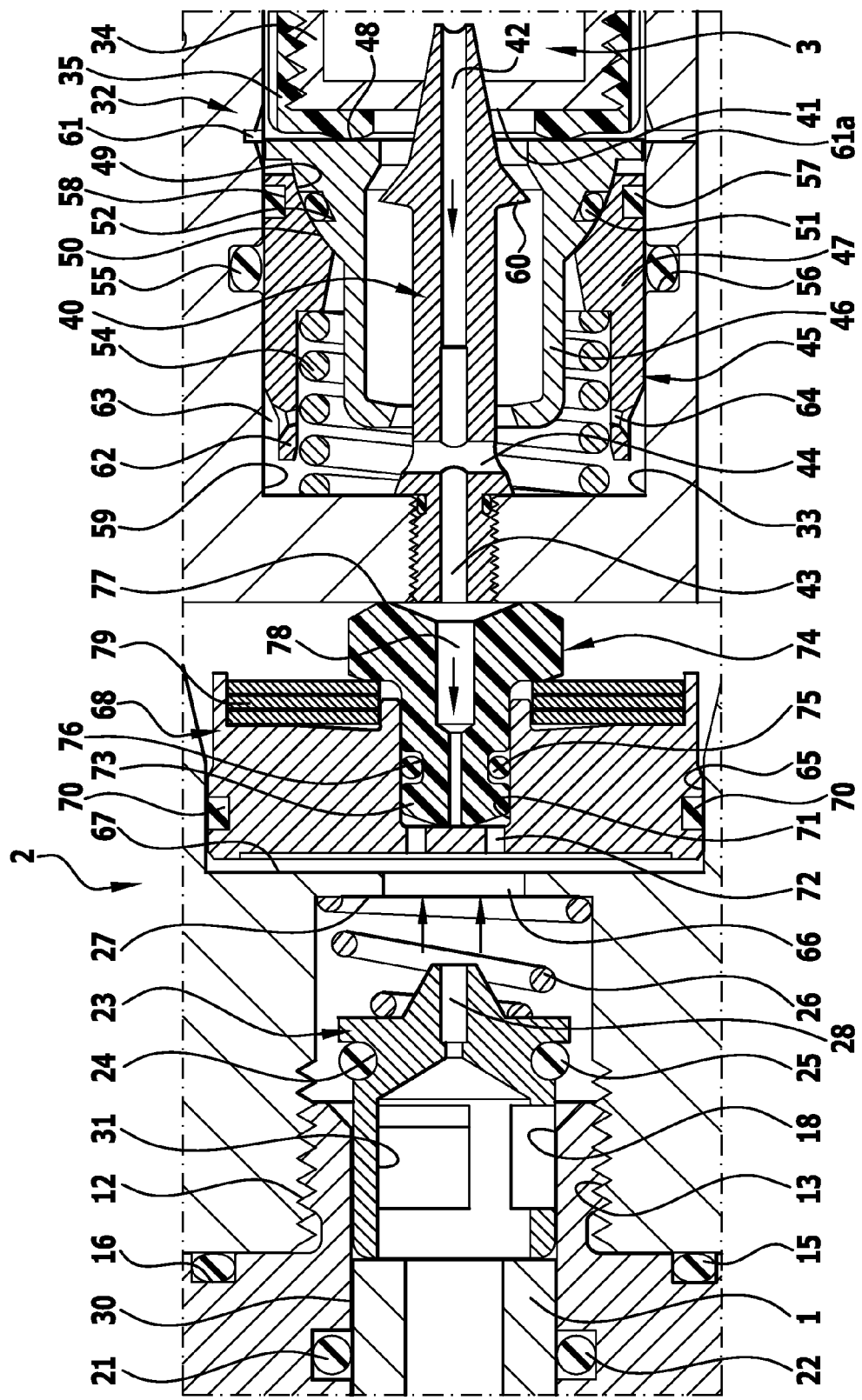
FIG. 4: a view similar to FIG. 3 with the regulating valve in the closed position thereof.
Figure 5:
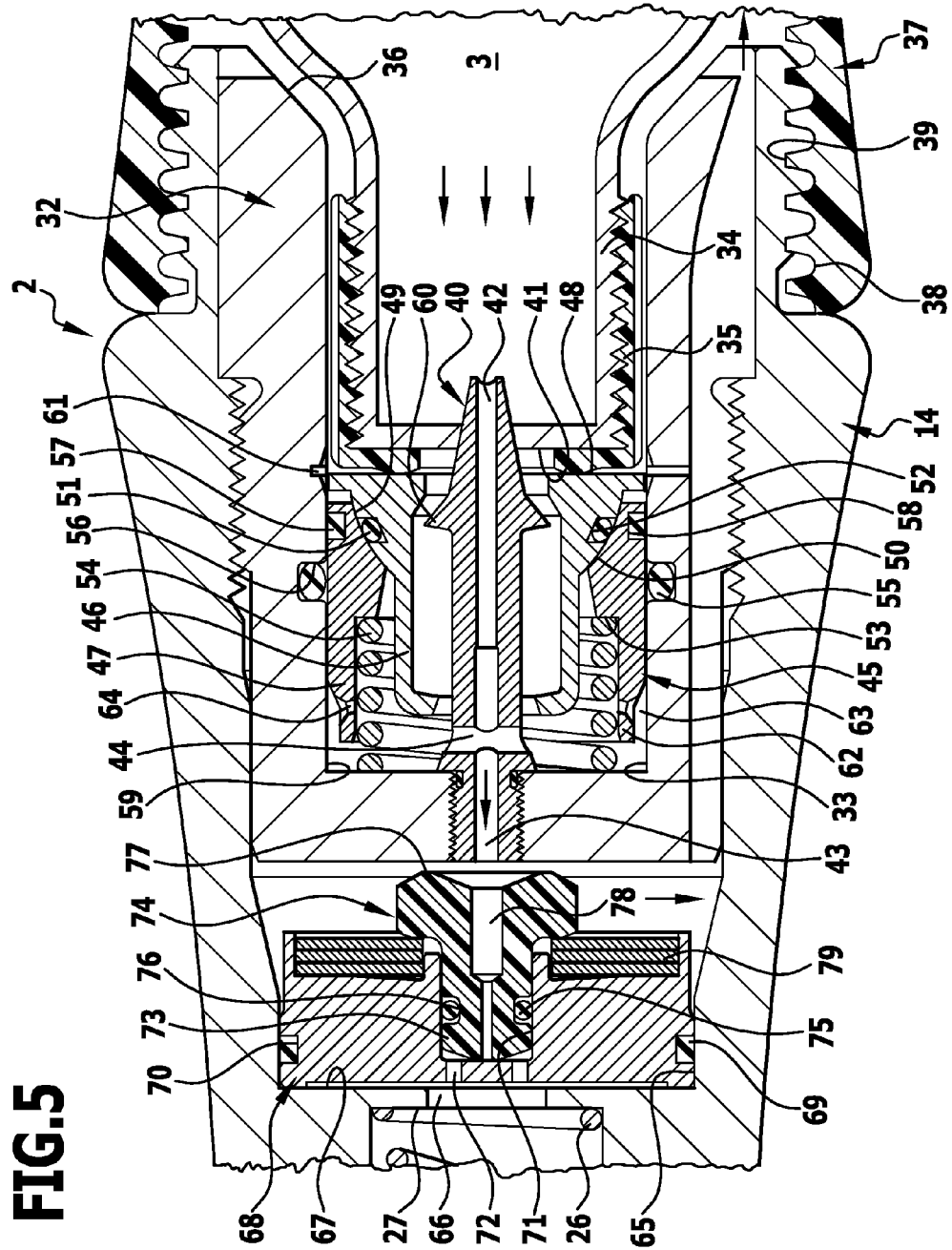
FIG. 5: a view similar to FIG. 3 with the connector element in the disengaged position.

If the pressure of the stream of gas flowing in the bearing chamber 65 downstream of the first ring seal 69 increases above a certain value, this will lead to a force acting on the valve body 68 which counteracts the spring action of the disc spring 79 since the part of the valve chamber 65 located upstream of the first ring seal 69 is not subjected to the compressed gas. Upon a certain gas pressure being exceeded, this leads to the valve body 68 being displaced, against the effect of the disc spring 70, towards the connector element 74 until the closed central region of the bearing chamber 71 abuts in sealing manner on the end face of the connector element 74 thereby blocking the flow channel 78 (FIG. 4). Consequently, a further inflow of gas from the compressed gas cartridge 3 is terminated, and opening of the valve body 68 will only occur again when the pressure prevailing downstream of the valve body 68 has diminished. The maximum pressure prevailing in the region downstream of the valve body 68 is limited in this way. The valve body 68 works as a pressure relief valve.

In normal operation, the connector element 74 always remains in sealing engagement with the seating body 32. If, however, the pressure in the compressed gas cartridge 3 exceeds the normal maximum pressure of the gas in the compressed gas cartridge, for example in the case of a sterilization process and the rise in temperature associated therewith, the force, which is exerted by the pressurised gas on the connector element 74 and which seeks to displace the connector element 74 in the direction of flow, can become so large that the connector element 74 is lifted off the rear face of the base of the connector shaft 33 against the effect of the disc spring 79 so that gas can now enter that section of the valve chamber 65 which is located upstream of the first ring seal 69, i.e. a ventilation process takes place in this region and there is a reduction in the excess pressure prevailing in the compressed gas cartridge 3 and in the following flow channel. Thus, the connector element 74 works as a safety valve which opens and thereby diminishes the excess pressure occurring when the maximum value of the pressure, which value lies significantly above the normal operating pressure, is exceeded.

In the case of a sterilization process, the connector 2 is normally separated from the connector fitting 1 so that the closure body 23 is located in its closed position. In consequence, the pressure prevailing downstream of the valve body 68 is normally the same as that prevailing upstream. Due to the different cross sections of the valve body 68 on the one hand and of the connector element 74 on the other, this leads to the connector element 74 abutting against the seating body 32 in sealing manner.

In the case of a rise in temperature, in the course of a sterilization process for example, the pressure downstream of the valve body 68 rises in accord with the normal temperature dependence of pressure, for gases, in proportion to the increase of temperature, whereas the pressure rises over-proportionately on the upstream side thereof. This is due to the fact that the compressed gas in the compressed gas cartridge is present in liquid form and, upon a rise in temperature, it reaches a supercritical state in which the rise in pressure occurring with the rise in temperature is very much greater than is the case for a pure gas. This increase of pressure at the upstream side of the valve body and the connector element finally leads to the connector element 74 being lifted off the seating body 32 when the ratio of the pressure upstream of the connector element 74 to the pressurised flow downstream of the valve body 68 becomes greater than the surface ratio which arises as a result of the different cross sections of the valve body 68 (diameter D) on the one hand and the connector element 74 (diameter d) on the other.

In connection therewith, both the valve body 68 and the connector element 74 are subjected to the action of the same disc spring 79 which primarily ensures that the valve body 68 is normally in the open position and the connector element 74 in the sealing position, the difference between the force of the disc spring 79 on the one hand and the force of the excess pressure that is effective respectively on the valve body 68 and the connector element 74 then being used for regulating the valve body 68 and the connector element 74.

Despite the measures for the sealing process that have been described, one cannot entirely exclude the possibility that in the connector region of the compressed gas cartridge 3, in the case of the sealing of the sealing cap 35 and the sealing surface 48, unwanted gas could escape laterally into the connector shaft 33. In order to prevent a build up of gas in this region, it is expedient for the sealing cap 35 to comprise channel-like depressions 80 in the lateral boundary region thereof through which the gas can flow past the sealing cap 35 to the exterior from the part of the connector shaft 33 which is sealed with respect to the section 59 of the connector shaft 33 by means of the sealing piece 45.

The invention claimed is:

1. A compressed gas operated instrument, comprising:
    a connector for a compressed gas cartridge to which the compressed gas cartridge is connectable in a sealed manner by a supply channel for a stream of compressed gas flowing out of the compressed gas cartridge, and
    a regulating valve in the supply channel which governs the stream of compressed gas flowing through the supply channel, the regulating valve comprising a valve body which is mounted in a valve chamber through which the supply channel extends, said valve body being displaceable in the valve chamber and sealed with respect to a wall of the valve chamber by means of a first seal, the valve body being connected on an upstream side thereof in a sealed manner to a connector element by means of a second seal and being displaceable with respect to the connector element by displacement thereof in the valve chamber, the connector element comprising a continuous flow channel and being connected at an inlet end thereof to the supply channel in a sealed manner, the valve body comprising a flow passage which is connected at a gas outlet end thereof to the supply channel located downstream of the valve chamber, the valve body being displaceable in the valve chamber against a direction of flow between an open position in which there is a flowing connection between the flow channel of the connector element and the flow passage of the valve body and a closed position in which the valve body is moved against an opening of the flow channel of the connector element thereby closing it, the valve body being biased in the direction of the open position by a spring element, and a cross-sectional area of the valve body surrounded by the first seal being larger than a cross-sectional area surrounded by the second seal, wherein:

the connector element is pressed by a spring element and by gas pressure downstream of the valve body into a sealing position in which the connector element tightly abuts against the supply channel entering the valve chamber and thereby connects said supply channel in a gas-tight manner to the flow channel in the connector element, the connector element is displaceable against the effect of the spring element from the supply channel into a disengaged position in which the supply channel entering the valve chamber is open into a part of the valve chamber that is located upstream of the first seal; and a ratio of the cross-sectional area of the valve body located downstream in the direction of flow with respect to the cross-sectional area of the connector element located upstream in the direction of flow is larger than a ratio of a gas pressure in the compressed gas cartridge to a regulated gas pressure downstream of the valve body at ambient temperature and is smaller than a ratio of these pressures at temperatures that are significantly higher compared to the ambient temperature.

2. An instrument in accordance with claim 1, wherein the spring element is a disc spring.

3. An instrument in accordance with claim 1, wherein:
the valve body comprises a central bearing chamber which is open at a gas inlet end and into which there projects a displaceable bearing stem of the connector element that is sealed by means of the second seal, and the flow passage emerges from the bearing chamber at the gas outlet end thereof.

4. An instrument in accordance with claim 1, wherein, in the closed position thereof, the valve body abuts a gas outlet end face of the connector element and thereby closes the flow channel.

5. An instrument in accordance with claim 1, wherein the spring element biasing the valve body into the open position and the spring element pressing the connector element into the sealing position is the same spring element.

6. An instrument in accordance with claim 1, wherein:
a closure body is mounted in the supply channel downstream of the regulating valve in a displaceable manner, said closure body being displaceable by a connector fitting that is inserted into the supply channel from a downstream side thereof from a closed position located downstream in the direction of flow into an open position located upstream in the direction of flow, the closure body unblocks the flow channel in the open position and blocks it in the closed position, and the closure body comprises a passage which permits a very much reduced current of the compressed gas to flow past the closure body even when the closure body is positioned in the closed position.

7. An instrument in accordance with claim 6, wherein the passage is a channel of small cross section passing through the closure body.

8. An instrument in accordance with claim 6, wherein the passage is formed by a porous wall region of the closure body.

9. An instrument in accordance with claim 6, wherein the closure body is biased in a direction of the closed position by a spring.

10. An instrument in accordance with claim 6, wherein, in the closed position thereof, the closure body is sealed with respect to the supply channel by a seal.

11. A compressed gas operated instrument, comprising:
a connector for a compressed gas cartridge to which the compressed gas cartridge is connectable in a sealed manner by a supply channel for a stream of compressed gas flowing out of the compressed gas cartridge, and a regulating valve in the supply channel which governs the stream of compressed gas flowing through the supply channel, the regulating valve comprising a valve body which is mounted in a valve chamber through which the supply channel extends, said valve body being displaceable in the valve chamber and sealed with respect to a wall of the valve chamber by means of a first seal, the valve body being connected on an upstream side thereof in a sealed manner to a connector element by means of a second seal and being displaceable with respect to the connector element by displacement thereof in the valve chamber, the connector element comprising a continuous flow channel and being connected at an inlet end thereof to the supply channel in a sealed manner, the valve body comprising a flow passage which is connected at a gas outlet end thereof to the supply channel located downstream of the valve chamber, the valve body being displaceable in the valve chamber against a direction of flow between an open position in which there is a flowing connection between the flow channel of the connector element and the flow passage of the valve body and a closed position in which the valve body is moved against an opening of the flow channel of the connector element thereby closing it, the valve body being biased in the direction of the open position by a spring element, and a cross-sectional area of the valve body surrounded by the first seal being larger than a cross-sectional area surrounded by the second seal, wherein:

a closure body is mounted in the supply channel downstream of the regulating valve in a displaceable manner, said closure body being displaceable by a connector fitting that is inserted into the supply channel from a downstream side thereof from a closed position located downstream in the direction of flow into an open position located upstream in the direction of flow, the closure body unblocks the flow channel in the open position and blocks it in the closed position, and the closure body comprises a passage which permits a very much reduced current of the compressed gas to flow past the closure body even when the closure body is positioned in the closed position.

12. An instrument in accordance with claim 11, wherein the spring element is a disc spring.

13. An instrument in accordance with claim 11, wherein:
the valve body comprises a central bearing chamber which is open at a gas inlet end and into which there projects a displaceable bearing stem of the connector element that is sealed by means of the second seal, and
the flow passage emerges from the bearing chamber at the gas outlet end thereof.

14. An instrument in accordance with claim 11, wherein the passage is a channel of small cross section passing through the closure body.

15. An instrument in accordance with claim 11, wherein the passage is formed by a porous wall region of the closure body.

16. An instrument in accordance with claim 11, wherein the closure body is biased in a direction of the closed position by a spring.

17. An instrument in accordance with claim 11, wherein, in the closed position thereof, the closure body is sealed with respect to the supply channel by a seal.

18. An instrument in accordance with claim 11, wherein:
the connector element is pressed by a spring element and by gas pressure downstream of the valve body into a sealing position in which the connector element tightly abuts against the supply channel entering the valve chamber and thereby connects said supply channel in a gas-tight manner to the flow channel in the connector element, and
the connector element is displaceable against the effect of the spring element from the supply channel into a disengaged position in which the supply channel entering the valve chamber is open into a part of the valve chamber that is located upstream of the first seal.

19. An instrument in accordance with claim 18, wherein a ratio of the cross-sectional area of the valve body located downstream in the direction of flow with respect to the cross-sectional area of the connector element located upstream in the direction of flow is larger than a ratio of a gas pressure in the compressed gas cartridge to a regulated gas pressure downstream of the valve body at ambient temperature and is smaller than a ratio of these pressures at temperatures that are significantly higher compared to the ambient temperature.

\* \* \* \* \*